United States Patent
Baker et al.

(10) Patent No.: US 10,774,021 B2
(45) Date of Patent: Sep. 15, 2020

(54) PROCESS FOR PREPARATION OF HYDROFLUOROALKENES BY SELECTIVE CATALYTIC CONSECUTIVE HYDRODEFLUORINATION

(71) Applicant: UNIVERSITY OF OTTAWA, Ottawa (CA)

(72) Inventors: Ralph Thomas Baker, Ottawa (CA); Nicholas Orlando Andrella, Ottawa (CA)

(73) Assignee: University of Ottawa, Ottawa (CA)

( * ) Notice: Subject to any disclaimer, the term of this patent is extended or adjusted under 35 U.S.C. 154(b) by 0 days.

(21) Appl. No.: 16/329,633

(22) PCT Filed: Aug. 30, 2017

(86) PCT No.: PCT/CA2017/051022
§ 371 (c)(1),
(2) Date: Feb. 28, 2019

(87) PCT Pub. No.: WO2018/039794
PCT Pub. Date: Mar. 8, 2018

(65) Prior Publication Data
US 2019/0194096 A1    Jun. 27, 2019

Related U.S. Application Data

(60) Provisional application No. 62/381,256, filed on Aug. 30, 2016.

(51) Int. Cl.
| | |
|---|---|
| C07C 17/23 | (2006.01) |
| C07C 21/18 | (2006.01) |
| C07C 41/24 | (2006.01) |
| C07F 1/08 | (2006.01) |
| B01J 31/24 | (2006.01) |
| B01J 31/00 | (2006.01) |
| B01J 31/02 | (2006.01) |
| C07C 43/17 | (2006.01) |

(52) U.S. Cl.
CPC .............. *C07C 17/23* (2013.01); *B01J 31/00* (2013.01); *B01J 31/0267* (2013.01); *B01J 31/2404* (2013.01); *C07C 41/24* (2013.01); *C07F 1/08* (2013.01); *B01J 2231/641* (2013.01); *B01J 2531/0222* (2013.01); *B01J 2531/16* (2013.01); *C07C 21/18* (2013.01); *C07C 43/17* (2013.01)

(58) Field of Classification Search
CPC combination set(s) only.
See application file for complete search history.

(56) References Cited

U.S. PATENT DOCUMENTS

2012/0126187 A1 *  5/2012  Low .................... C11D 7/5009
                                          252/602

OTHER PUBLICATIONS

Peterson, A. A. et al. "Phosphinorhodium-Catalyzed Dehalogenation of Chlorinated and Fluorinated Ethylenes: Distinct Mechanisms with Triethylsilane and Dihydrogen" Organometallics 2009, 28, 5982-5991 (Year: 2009).*
Kuehnel, M. F. et al. "Titanium-Catalyzed Vinylic and Allylic C_F Bond Activation—Scope, Limitations and Mechanistic Insight" Chem. Eur. J. 2012, 18, 10701-10714 (Year: 2012).*

* cited by examiner

*Primary Examiner* — Medhanit W Bahta
(74) *Attorney, Agent, or Firm* — Hoffmann & Baron, LLP

(57) ABSTRACT

The present application provides a hydrodefluorination process for the preparation of hydrofluoroalkenes by catalyzed substitution of one or more F atoms of a C2-C30 fluoroalkene, or a C2-C10 fluoroalkene, with one or more H atoms using a hydride source, such as a silane, and copper catalyst. During this process at least one C—F bond in the fluoroakene is converted to a C—H bond. The process is useful in the manufacture of hydrofluoroalkenes, such as hydrofluoroalkenes employed as, for example, refrigerants and blowers. Also provided are precatalyst compositions for performing the process, and formulations manufactured from hydrofluoroalkenes produced using the process.

10 Claims, 10 Drawing Sheets

PROCESS FOR PREPARATION OF HYDROFLUOROALKENES BY SELECTIVE CATALYTIC CONSECUTIVE HYDRODEFLUORINATION

This application is the U.S. National Phase of, and Applicant claims priority from, International Patent Application Number PCT/CA2017/051022 filed Aug. 30, 2017, which claims priority from U.S. Provisional Application Ser. No. 62/381,256 filed Aug. 30, 2016, each of which is incorporated herein by reference.

FIELD OF THE INVENTION

The present application pertains to the field of catalysis. More particularly, the present application relates to a hydrodefluorination catalyst, a catalytic hydrodefluorination process and products thereof.

INTRODUCTION

Fluorocarbon-based fluids have found widespread use in many commercial and industrial applications. For example, fluorocarbon-based fluids are frequently used as working fluids in systems such as air conditioning, heat pump and refrigeration applications.

Certain fluorocarbons have been a preferred component in many heat exchange fluids, such as refrigerants, for many years in many applications. For, example, fluoroalkanes, such as chlorofluoromethane and chlorofluoroethane derivatives, have gained widespread use as refrigerants in applications including air conditioning and heat pump applications owing to their unique combination of chemical and physical properties.

Concern has increased in recent years about potential damage to the earth's atmosphere and climate, and certain chlorine-based compounds have been identified as particularly problematic in this regard. The use of chlorine-containing compositions (such as chlorofluorocarbons (CFCs), hydrochlorofluorocarbons (HCFCs) and the like) as refrigerants in air-conditioning and refrigeration systems has become disfavored because of the ozone-depleting properties associated with many of such compounds. There has thus been an increasing need for new fluorocarbon and hydrofluorocarbon compounds and compositions that offer alternatives for refrigeration and heat pump applications.

It is generally considered important, however, that any potential substitute refrigerant also possess those properties present in many of the most widely used fluids, such as excellent heat transfer properties, chemical stability, low- or no-toxicity, non-flammability and lubricant compatibility, among others. Hydrofluoroalkenes have been found to have particular value as substitute refrigerant compounds. However, to date, there is no efficient process that minimizes environmental toxicity for the synthesis of such compounds.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present application is to provide a process for preparation of hydrofluoroalkenes by selective catalytic consecutive hydrodefluorination. In accordance with an aspect of the present application, there is provided a process for hydrodehalogenation of a fluoroalkene comprising treating a fluoroalkene with a hydride source and a catalyst of Formula VIII $$L_xM_yH_z \qquad \text{VIII}$$

where L is a monodentate, bidentate, tridentate, tetradentate phosphorous, nitrogen, oxygen, sulfur or carbon-based ligand or combination thereof, of the general formula $PR_3$, $NR_3$, $SR_2$, $OR_2$, $:CR_2$ (carbene) where each R is independently; H, Alk(alkyl), Ar(aryl), $SiR_3$ (silyl), OR (alkoxy), $NR_2$ (amino) or halogen. For example: $P(OEt)_3$, $PPh_3$, $PCp_3$, Bipy, Phen, tmeda, Triphos, Diphos, 1,2-bis(diphenylphosphino)benzene, IPr (1,3-bis(2,6-diisopropylphenyl)-imidazol-2-ylidene), SIMes (1,3-bis(2,4,6-trimethylphenyl)-2-imidazolidinylidene);

M is a metal, such as a Group 11 metal, for example, $Cu^I$ or $Cu^{II}$; and x is an integer from 1 to 4;

y is 1;

z is an integer from 1 to 4; and the sum of z+x is less than or equal to 4.

In accordance with another aspect, there is provided a compound of Formula IX

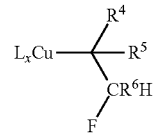

IX where each of $R^4$. $R^5$ and $R^6$ are each independently H, halogen, alkyl, alcohol (OH), ether (OR), amine ($NR_3$), thiol (SH), thioether (SR), fluorothioether, silyl, allene ($=CR_2$), vinyl ($-C(R)=CR_2$), alkynyl ($-C\equiv CR$), phenyl (Ph), carbonyl ($-C(O)R$), aldehyde ($-C(O)H$), carbonate ($-OC(O)OR$), ester ($-C(O)OR$), nitrile ($-C\equiv N$), isonitrile ($-N\equiv C$), nitro ($-NO_2$), pyridyl ($-C_5H_4N$), sulfinyl ($-S(O)R$), sulfonyl ($-S(O)_2R$), thiocyanate ($-SC\equiv N$), boronate ($-B(OR)_2$), and their fluorovariants respectively, and L is a monodentate, bidentate, tridentate, tetradentate phosphorous, nitrogen, oxygen, sulfur or carbon-based ligand or combination thereof, of the general formula $PR_3$, $NR_3$, $SR_2$, $OR_2$, $:CR_2$ (carbene) where each R is independently; H, Alk(alkyl), Ar(aryl), $SiR_3$ (silyl), OR (alkoxy), $NR_2$ (amino) or halogen. For example: $P(OEt)_3$, $PPh_3$, $PCp_3$, Bipy, Phen, tmeda, Triphos, Diphos, 1,2-bis(diphenylphosphino)benzene, IPr (1,3-bis(2,6-diisopropylphenyl)-imidazol-2-ylidene), SIMes (1,3-bis(2,4,6-trimethylphenyl)-2-imidazolidinylidene).

In accordance with another aspect, there is provided a liquid composition comprising a hydrofluoroalkene produced using a hydrodefluorination process as described herein. The liquid composition comprising additional components, such as, but not limited to one or more additional hydrofluoroalkenes, hydrofluoroolefins, hydrochlorofluoroolefins and/or water and/or $CO_2$.

In accordance with another aspect, there is provided a precatalyst compostion comprising $((PPh_3)CuH)_6$ (or the like), one or more ligands, and $Cu^I$ or $Cu^{II}$ in a solvent, wherein each of the one or more ligands is, independently, a monodentate, bidentate, tridentate, or tetradentate, phosphorous, nitrogen, oxygen, sulfur or carbon-based ligand or combination thereof, of the general formula $PR_3$, $NR_3$, $SR_2$, $OR_2$, :$CR_2$ (carbene) where each R is independently; H, Alk(alkyl), Ar(aryl), $SiR_3$ (silyl), OR (alkoxy), $NR_2$ (amino) or halogen. For example: $P(OEt)_3$, $PPh_3$, $PCp_3$, Bipy, Phen, tmeda, Triphos, Diphos, 1,2-bis(diphenylphosphino)benzene, IPr (1,3-bis(2,6-diisopropylphenyl)-imidazol-2-ylidene), SIMes (1,3-bis(2,4,6-trimethylphenyl)-2-imidazolidinylidene).

BRIEF DESCRIPTION OF TABLES AND FIGURES

For a better understanding of the application as described herein, as well as other aspects and further features thereof, reference is made to the following description which is to be used in conjunction with the accompanying drawings, where:

Figure 9:
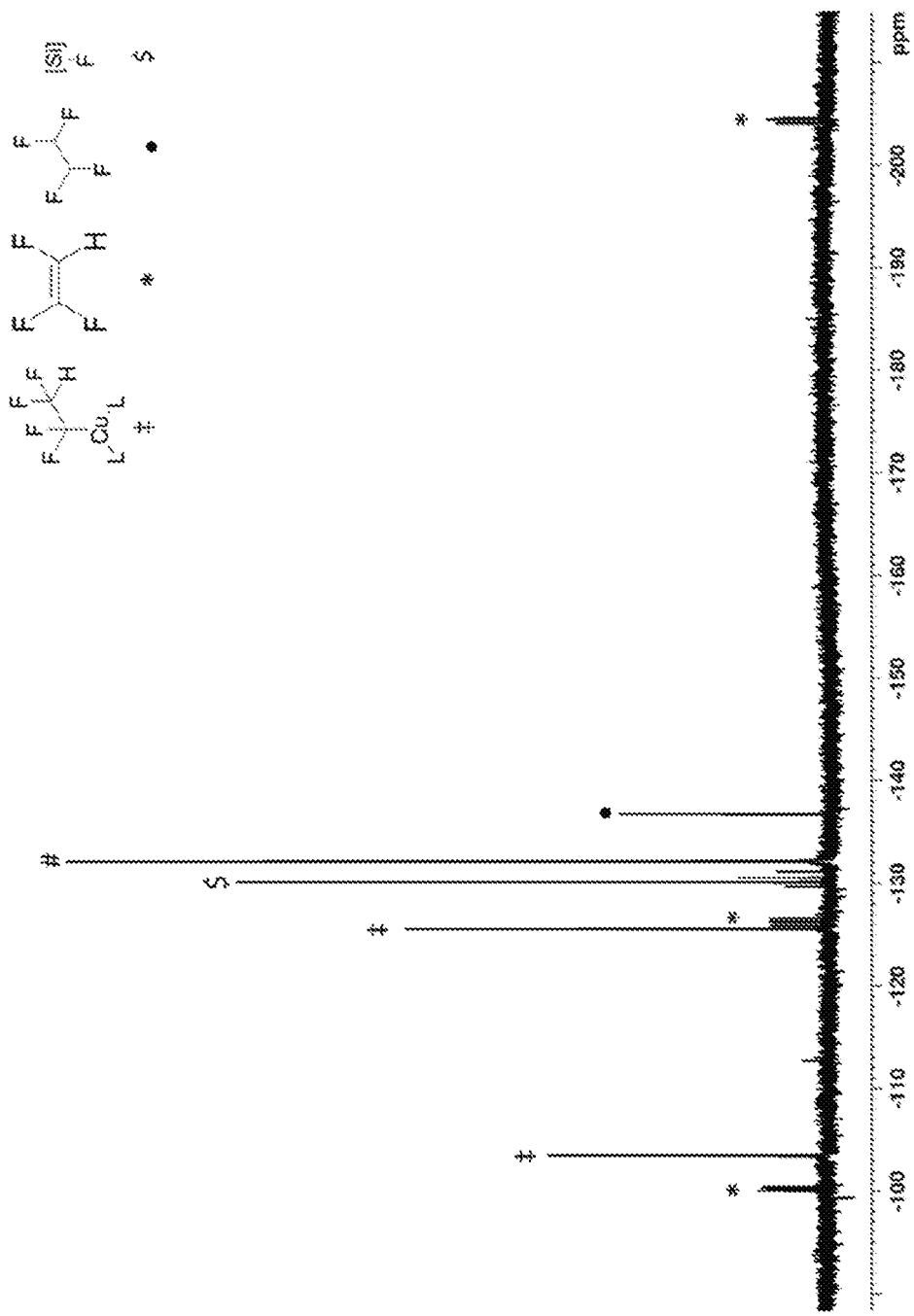
Figure 10:
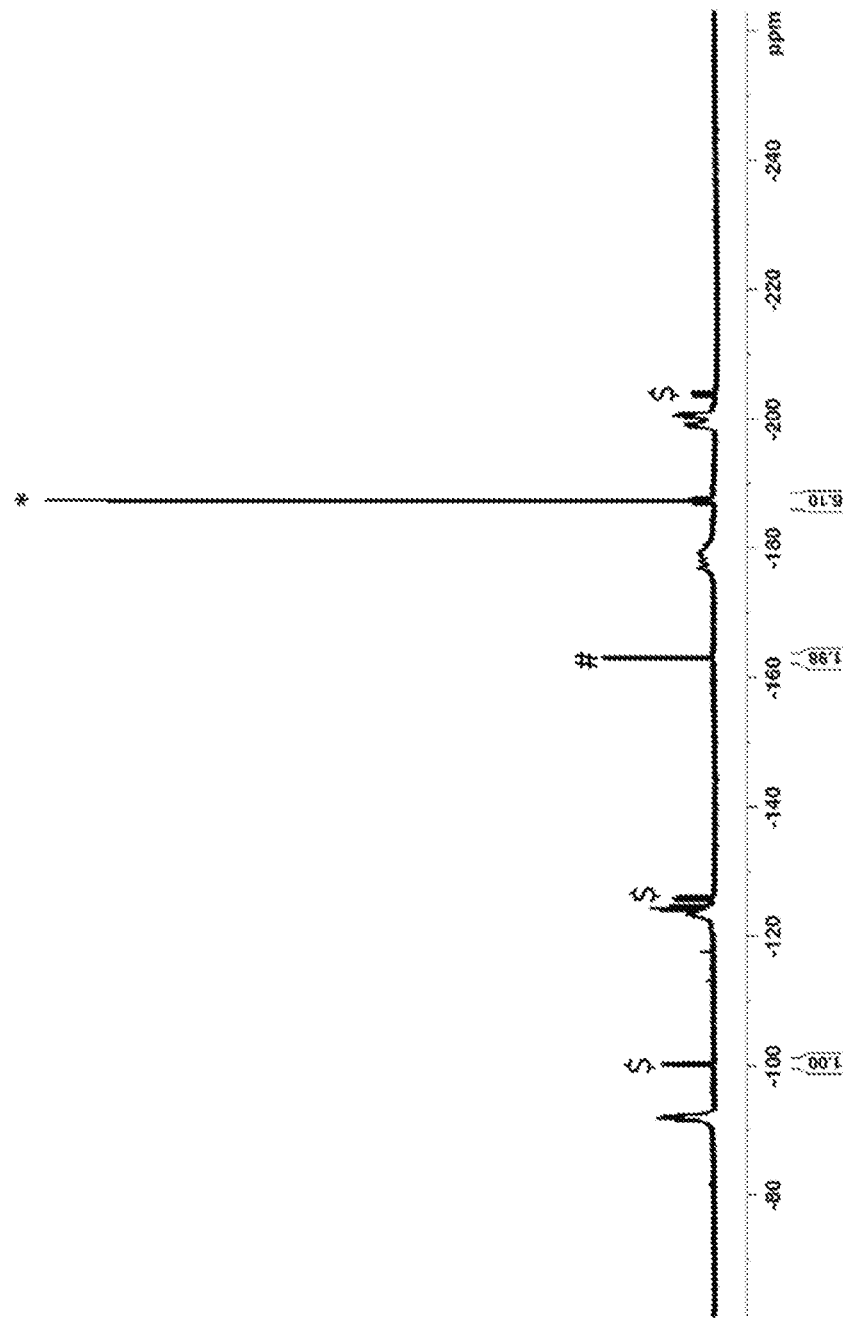

FIG. 9 depicts an $^{19}F$ NMR spectrum (282 MHz, $C_6D_6$) of the reaction of [Cu]—H with tetrafluoroethylene, where TMDS was the source of hydride (#=tetrafluoroethylene, *=trifluoroethylene, ●=1,1,2,2-tetrafluoroethane); and FIG. 10 depicts an $^{19}F$ NMR spectrum (282 MHz, $C_6D_6$) of a hydrodefluorination of iodotrifluoroethylene using [Cu]—H 1,2-bis(diphenylphosphino)ethane with and Red-Al as the hydride source ($=HTFE, #=cis-1,2-difluoroethylene and *=trans-1,2-difluoroethylene).

DETAILED DESCRIPTION

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, the term "alkyl" as a group or part of a group means a straight chain or, where available, a branched chain alkyl moiety or a cyclic alkyl moiety. For example, it may represent a $C_{1-12}$ alkyl function or a $C_{1-4}$ alkyl function, as represented by methyl, ethyl, n-propyl, i-propyl, n-butyl, s-butyl and t-butyl.

The term "alkenyl" as used herein includes straight-chained, branched and cyclic alkenyl groups, such as vinyl and allyl, groups.

The term "halogen" herein means a fluorine, chlorine, bromine or iodine atom.

As used herein the term "fluoroalkene" refers to any alkene where at least one C—H bond has been exchanged for a C—F bond.

The present application provides a hydrodefluorination process for the preparation of hydrofluoroalkenes by catalyzed substitution of one or more F atoms of a C2-C30 fluoroalkene, or a C2-C10 fluoroalkene, with one or more H atoms using a hydride source, such as a silane, and copper catalyst. During this process at least one C—F bond in the fluoroakene is converted to a C—H bond. The process is useful in the manufacture of hydrofluoroalkenes, such as hydrofluoroalkenes employed as, for example, refrigerants and blowing agents. Previous methods for synthesis of such hydrofluoroalkenes are typically expensive, time consuming and/or they involve the use of hazardous or environmentally damaging chemicals. The presently provided catalytic process is efficient and makes use of readily available, innocuous reagents.

The process is summarized in Scheme 1, where a compound of Formula I is hydrodehalogenated to form a compound of Formula IIa or IIb or a mixture thereof:

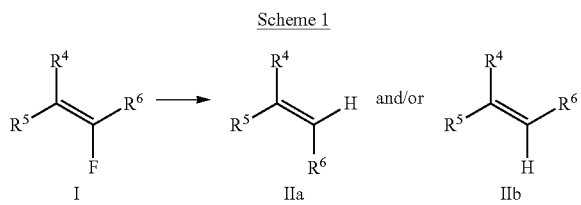

Scheme 1 where each of $R^4$, $R^5$ and $R^6$ are each independently H, halogen, alkyl, alcohol (OH), ether (OR), amine ($NR_3$), thiol (SH), thioether (SR), fluorothioether, silyl, allene (=$CR_2$), vinyl (—C(R)=$CR_2$), alkynyl (—C≡CR), phenyl (Ph), carbonyl (—C(O)R), aldehyde (—C(O)H), carbonate (—OC(O)OR), ester (—C(O)OR), nitrile (—C≡N), isonitrile (—N≡C), nitro (—$NO_2$), pyridyl (—$C_5H_4N$), sulfinyl (—S(O)R), sulfonyl (—S(O)$_2$R), thiocyanate (—SC≡N), boronate (—B(OR)$_2$), and their fluorovariants respectively, where R is alkyl, alkenyl, aryl, silyl, alkoxy, amino, or halogen, or wherein R is an, optionally substituted, alkyl or alkenyl group.

In one embodiment, the starting fluorinated compound includes more than one F substituent. In the case in which the starting compound is a compound of Formula Ia, which includes two F substituents, the reaction can be summarized as in Scheme 2:

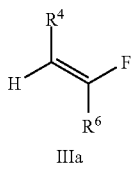

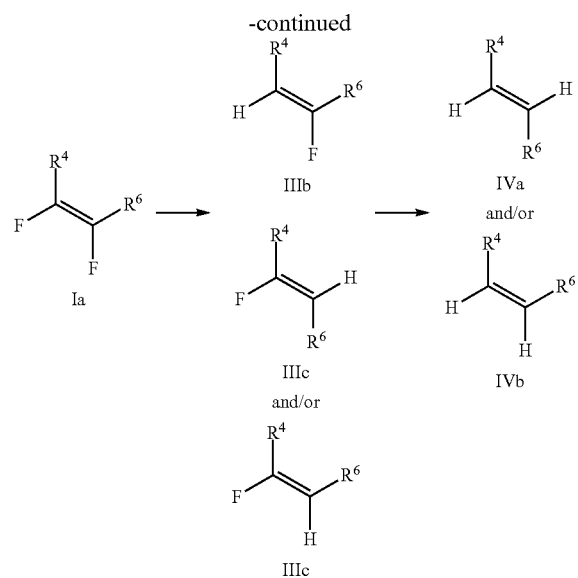

In this example, depending on the conditions of the reaction, the reaction proceeds to monohydrodefluorination of the compound of Formula Ia, or dihydrodefluorination of the compound of Formula Ia. In some examples, the reaction product is a mixture of both the mono- and dihydrodefluorination products. Alternatively, reaction conditions can be tuned to selectively produce one or more of the specific mono- or dihydrodefluorination products. In general, bulky phosphine ligands yield monohydrodefluorination products, bidentate phosphine ligands are selective for di/tri hydrodefluorination with some dependence on the bite-angle, and alkyl phosphites are unselective (i.e. the number of hydrodefluorinations is limited only by the amount of silane present).

In another embodiment, the starting fluorinated compound comprises more than two F substituents. In the case in which the starting compound is a compound of Formula Ib, which includes three F substituents, the reaction can be summarized as in Scheme III:

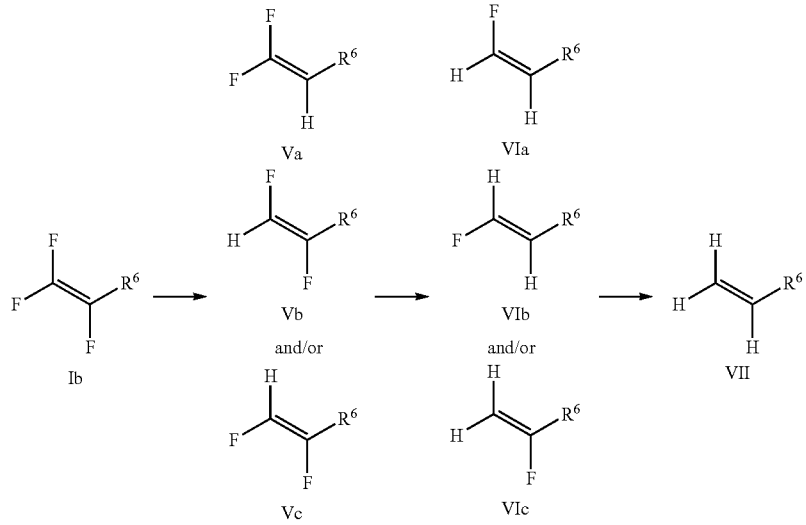

In this example, depending on the conditions of the reaction, the reaction proceeds to monohydrodefluorination of the compound of Formula Ib, dihydrodefluorination of the compound of Formula Ib or trihydrodefluorination of the compound of Formula Ib. In some examples, the reaction product is a mixture of the mono-, di- and trihydrodefluorination products. Alternatively, reaction conditions can be tuned to selectively produce one or more of the specific mono-, di- or trihydrodefluorination products. In general, aryl phosphines favor mono-hydrodefluorination in the presence of LiI, and bidentate phosphines and NHCs favor dihydrodefluorination.

As would be readily appreciated by a worker skilled in the art, if the substituents in the compound of Formula I comprise additional fluorine groups, the process of the present application can proceed to multiply hydrodefluorinated products. Tuning of the reaction facilitates production of the hydrodefluorinated product, or mixture of products, of interest.

The reaction of Scheme 1 (and Schemes 2 and 3) is catalyzed using $L_xM_yH_z$ using a stoichiometric amount of silane $[R^1R^2R^3SiH]$, based on the amount of the starting fluorinated compound (based on the F content of the starting fluoroalkene), as the hydride source with concomitant formation of $[R^1R^2R^3SiF]$ as the reaction progresses. In practice, the amount of silane added to the reaction is at least stoichiometric; however, the silane can be added in stoichiometric excess. Without wishing to be bound by theory, it is proposed that the reaction proceeds according to the reaction pathway shown in Scheme 4, where the catalyst is a copper catalyst:

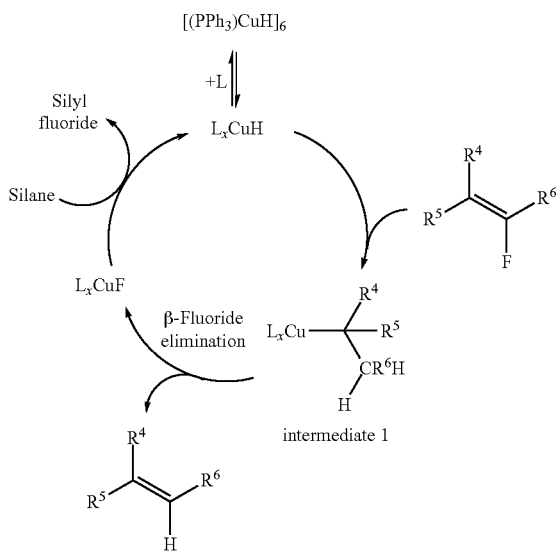

Scheme 4

Although the reaction scheme shown above indicates that the hydride source is a silane, it should be understood that alternative H sources can also be used (e.g., $H_2$ and base).

The present application further provides the catalyst of Formula VIII $$L_x M_y H_z \qquad \text{VIII}$$

where each L is a monodentate, bidentate, tridentate, or tetradentate phosphorous, nitrogen, oxygen, sulfur or carbon-based ligand or combination thereof, of the general formula $PR_3$, $NR_3$, $SR_2$, $OR_2$, $:CR_2$ (carbene) where each R is independently; H, Alk (alkyl), Ar (aryl), $SiR_3$ (silyl), OR (alkoxy), $NR_2$ (amino) or halogen (for example each L can be, independently, P(OEt)$_3$, PPh$_3$, PCp$_3$, Bipy, Phen, tmeda, Triphos, Diphos, 1,2-bis(diphenylphosphino)benzene, IPr (1,3-bis(2,6-diisopropylphenyl)-imidazol-2-ylidene), or SIMes (1,3-bis(2,4,6-trimethylphenyl)-2-imidazolidinylidene)).

M is a metal, such as a Group 11 metal, for example, $Cu^I$ or $Cu^{II}$; and x is an integer from 1 to 4;

y is 1;

z is an integer from 1 to 4; and the sum of z+x is less than or equal to 4.

Examples of the catalyst used in the present process include, but are not limited to, (PPh$_3$)$_3$CuH or (PPh$_3$)$_2$CuH. These examples do not form clusters, however, complexes that do cluster can also be employed as the catalyst.

In one embodiment, the reaction is catalyzed by $L_x M_y H_z$ using a stoichiometric amount of silane [$R^1R^2R^3$SiH] as the source of H, with concomitant formation of [$R^1R^2R^3$SiF] as the reaction progresses. The catalyst can be used as Stryker's reagent/Osborne complex [((PPh$_3$)CuH)$_6$— hexameric in the solid state] with an additional L, or generated in situ by a) addition of $Cu^I$ or $Cu^{II}$, L and the recommended silane or b) addition of $Cu^I$ or $Cu^{II}$, base (e.g., potassium tertiary butoxide) and $H_2$. The copper to ligand molar ratio can be in the range of 1:1-10, 1:2-10, or about 1:1.

Accordingly, the present application also provides a precatalyst composition comprising ((PPh$_3$)CuH)$_6$, at least one ligand and $Cu^I$ or $Cu^{II}$ in a solvent, wherein each of the at least one ligands is as defined above. In an alternative embodiment, the precatalyst composition comprises ((PPh$_3$)CuH)$_6$, or related complex derived from L and a $Cu^I$ or $Cu^{II}$ salt in situ, a base and $H_2$ in a solvent. The precatalyst compostion optionally also contains the silane, $R^1R^2R^3$SiH, or the silane is added after formation of the catalyst.

The substituents of the silane, $R^1$, $R^2$, $R^3$ are each independently H, Alk(alkyl), Ar(aryl), $SiR_3$ (silyl), OR (alkoxy), $NR_2$ (amino) or halogen. The silane used is preferentially water- and oxygen-tolerant with low volatility, which simplifies isolation and purification of desired products. In one non-limiting example, the silane is polymethylhydrosiloxane (PMHS).

Catalytic Reaction Process

The reaction is executed in a solvent of low-volatility and adequate polarity (For example, but not limited to: diethyl ether, benzene, toluene, xylenes, tetrahydrofuran, dimethoxyethane, acetonitrile, 1,4-dioxane, dimethylformamide, dimethylsulfoxide or sulfolane) to render the environment homogeneous. A solvent having adequate polarity, in the case in which the catalyst is a copper catalyst, is a solvent that is capable of dissolving CuH or other copper sources.

The reaction temperature is dependent on the solvent selected and the decomposition temperature of the catalyst, as would be readily appreciated by a worker skilled in the art. In one example, the reaction can be carried out in the temperature range from about 20-280° C., or from about 20-100° C.

In one example, the present catalytic process is useful, for example, in the synthesis of hydrofluoroalkenes such as, Z-1,2,3,3,3-pentafluoroprop-1-ene [HFO-1225ye], E-1,2,3,3,3-pentafluoroprop-1-ene [HFO-1225ye(E)], 2,3,3,3-tetrafluoroprop-1-ene [HFO-1234yf], 1,3,3,3-tetrafluoropropene [HFO-1234ze(E)] or 1,1-difluoropropene [HFO-1252zc] from hexafluoropropene [HFP]. These hydrofluoralkenes are generally effective and exhibit utility in refrigerant compositions, blowing agent compositions, compatibilizers, aerosols, propellants, fragrances, flavor formulations, and solvent compositions (see, for example, U.S. Patent publication 20160017231, which is incorporated herein by reference).

As noted above, this reaction can be tuned in order to select for products of interest. By way of example, it has been found that use of PAr$_3$ (Ar=any aryl substituent) as a ligand on the catalyst produces a mixture of HFO-1225ye (E)ze:HFO-1225ye in a molar ratio of 2:1. Use of PAlk$_3$ (Alk=any alkyl substituent, e.g. tBu—tertiary butyl) as a ligand produces a mixture of HFO-1225ye(E):HFO-1234yf in a molar ratio of 1:1. Further, use of phosphite P(OR)$_3$ (OR=any alkoxy substituent, e.g. OEt—ethoxy) as a ligand produces a mixture of HFO-1234ze(E): HFO-1234yf in a molar ratio of 1:7.

Compositions

The present application also provides compositions comprising a solvent or diluent and one or more hydrofluoroalkene produced by a process comprising hydrodehalogenating a C2-30 hydro(halo)fluoroalkene in the presence of a catalyst, such as a copper catalyst, and a silane.

In certain examples, compositions of the present application have a Global Warming Potential (GWP) of not greater than about 1000, more preferably not greater than about 500, and even more preferably not greater than about 150. In certain embodiments, the GWP of the present compositions is not greater than about 100 and even more preferably not greater than about 75. As used herein, "GWP" is measured relative to that of carbon dioxide and over a 100-year time horizon, as defined in "The Scientific Assessment of Ozone Depletion, 2002, a report of the World Meteorological Association's Global Ozone Research and Monitoring Project," which is incorporated herein by reference.

In certain examples, the present compositions also have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

The amount of the hydrofluoroalkene compounds, such as, for example HFO-1234, contained in the present compositions can vary widely, depending on the particular application, and compositions containing more than trace amounts and less than 100% of the compound are within broad the scope of the present application. Moreover, the compositions of the present application can be azeotropic, azeotrope-like or non-azeotropic. In certain examples, the present compositions comprise HFO-1234, for example HFO-1234ze, in amounts from about 5% by weight to about 99% by weight, or from about 5% to about 95%. Many additional compounds can be included in the present compositions. In certain embodiments, the present compositions include, in addition to HFO-1234ze, one or more of the following:

Difluoromethane (HFC-32)

Pentafluoroethane (HFC-125)

1,1,2,2-tetrafluoroethane (HFC-134)

1,1,1,2-Tetrafluoroethane (HFC-134a)

Difluoroethane (HFC-152a)

1,1,1,2,3,3,3-Heptafluoropropane (HFC-227ea)

1,1,1,3,3,3-hexafluoropropane (HFC-236fa)

1,1,1,3,3-pentafluoropropane (HFC-245fa)

1,1,1,3,3-pentafluorobutane (HFC-365mfc)

water $CO_2$

The relative amount of any of the above noted components, as well as any additional components which may be included in present compositions, can vary widely within the general broad scope of the present invention according to the particular application for the composition, and all such relative amounts are considered to be within the scope hereof.

To gain a better understanding of the invention described herein, the following examples are set forth. It should be understood that these examples are for illustrative purposes only. Therefore, they should not limit the scope of this invention in any way.

EXAMPLES

Example 1: Hydrofluoroalkene Production from Hexafluoropropene [HFP]

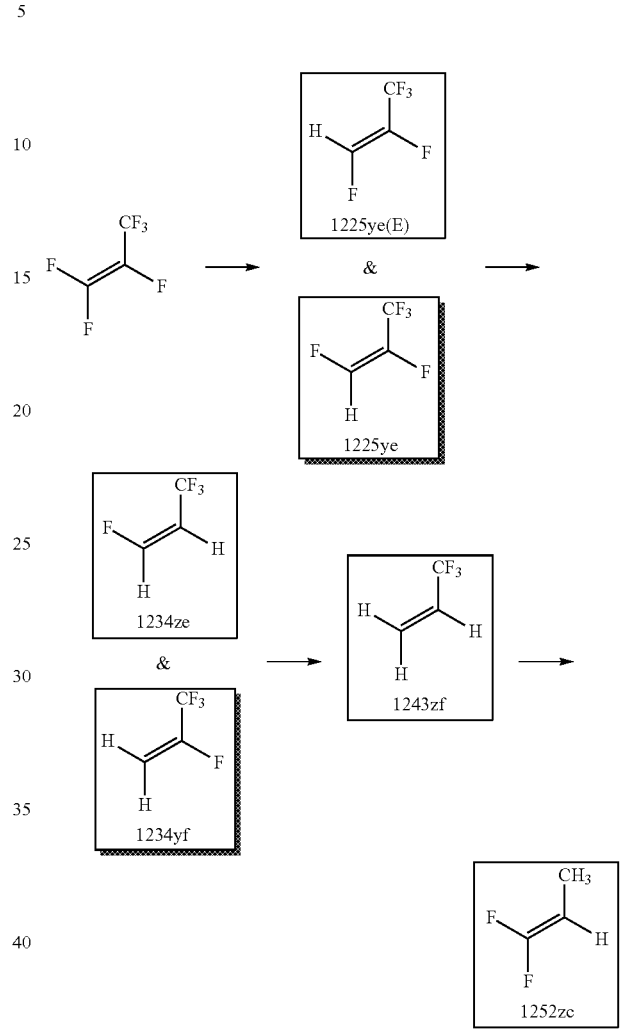

Reaction Using Cu—PPh$_3$ without Silane

Figure 1:
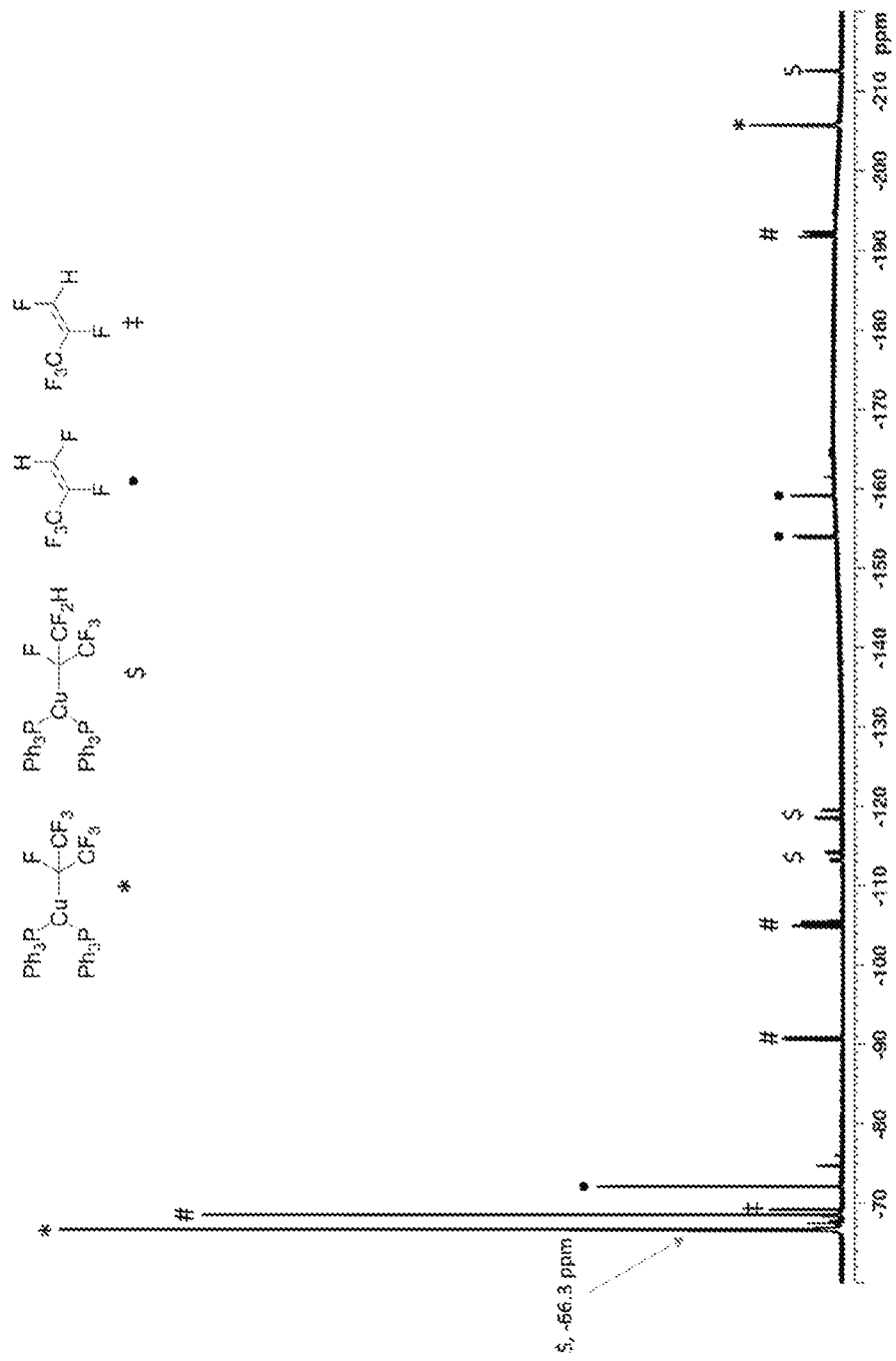
FIG. 1 depicts an $^{19}F$ NMR spectrum (282 MHz, $C_6D_6$) of the reaction of [Cu]—H with hexafluoropropene without silane (#=hexafluoropropene)

The deep red complex [(PPh$_3$)CuH]$_6$ (0.020 g, 0.010 mmol or 0.061 mmol of H$^-$) and triphenylphosphine (0.160 g, 0.61 mmol) were placed in an NMR tube, dissolved in 0.6 mL of benzene-d$_6$ [C$_6$D$_6$] and capped with a rubber septum. Gaseous hexafluoropropene [HFP] (3 mL, 1 atm) was then injected into the mixture and left to sit at 25° C. for 1 hours. The reaction mixture was then analyzed by $^{19}$F NMR. The results are depicted in FIG. 1, which demonstrates production of the cis and trans forms of the mono-hydrodefluorinated product. The copper-containing intermediate was also observed by NMR.

Reaction with Excess PPh$_3$ and Dimethylphenylsilane

Figure 2:
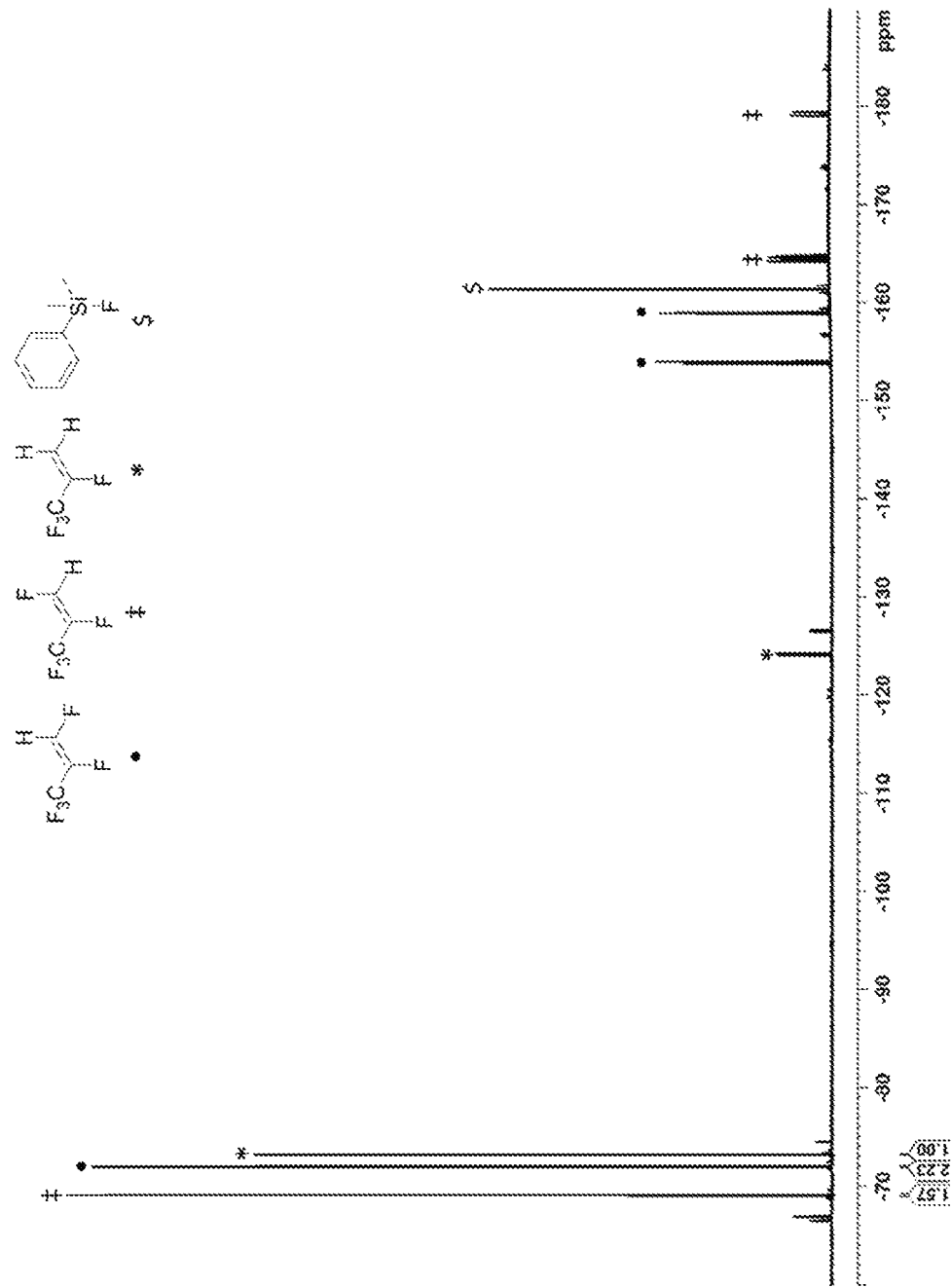
FIG. 2 depicts an $^{19}F$ NMR spectrum (282 MHz, $C_6D_6$) of the reaction of [Cu]—H with hexafluoropropene, where triphenylphosphine was used as ligand choice and dimethylphenylsilane as the source of hydride.

[(PPh$_3$)CuH]$_6$ (0.020 g, 0.010 mmol or 0.061 mmol of H$^-$), triphenylphosphine (0.160 g, 0.61 mmol) and dimethylphenylsilane (0.083 g, 0.61 mmol) were placed in an NMR tube, dissolved in 0.6 mL of benzene-d$_6$ [C$_6$D$_6$] and capped with a rubber septum. Gaseous HFP (3 mL, 1 atm) was then injected into the mixture and left to sit at 25° C. for ~3 hours. The reaction mixture was then analyzed by $^{19}$F NMR (see FIG. 2), which demonstrated >99% conversion of HFP. The normalized molar ratio of product distribution:1225ye(E): 1225ye:1234yf, was 2.2:1.6:1, respectively.

Reaction with Excess PPh$_3$ and PMHS

Figure 3:
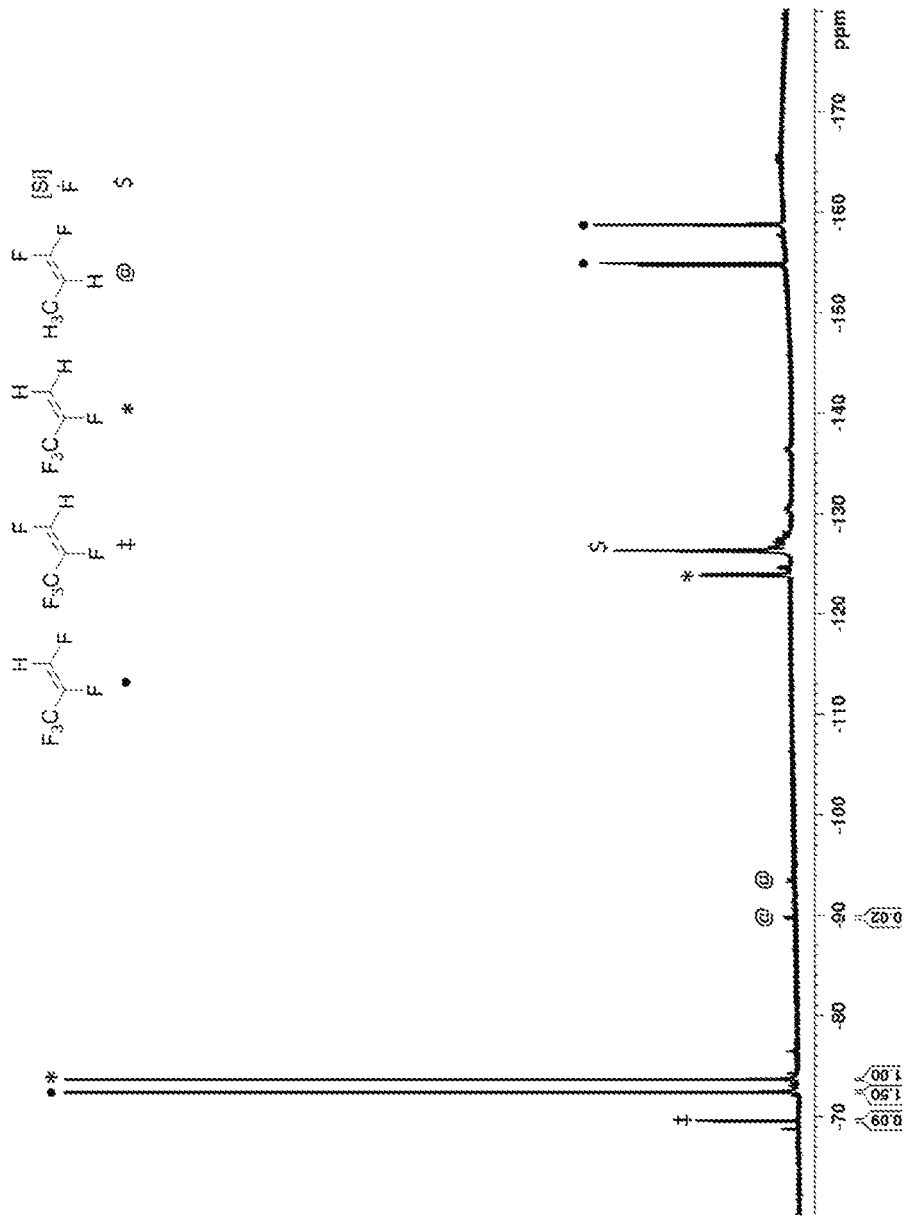
FIG. 3 depicts an $^{19}F$ NMR spectrum (282 MHz, $C_6D_6$) of the reaction of [Cu]—H with hexafluoropropene, where triphenylphosphine was used as ligand choice and PMHS as the source of hydride.

[(PPh$_3$)CuH]$_6$ (0.020 g, 0.010 mmol or 0.061 mmol of H$^-$) and triphenylphosphine (0.160 g, 0.61 mmol) were placed in an NMR tube, dissolved in 0.3 mL of benzene-d$_6$ [C$_6$D$_6$]/0.3 mL of polymethylhydroxysilane [PMHS] and capped with a rubber septum. HFP (3 mL, 1 atm) was then injected into the mixture and left to sit at 25° C. for 10 minutes, after which point it was heated to 80° C. for 30 minutes. The reaction mixture was then analyzed by $^{19}$F NMR (see FIG. 3), which demonstrated >99% conversion of HFP. The normalized molar ratio of product distribution of 1225ye(E):1234yf was 1.5:1, respectively. Trace amounts of 1225ye and (1,1-Difluoropropene) 1252zc were also observed.

Reaction with Excess TMDS Vs HFP w/Out Added Ligand

Figure 4:
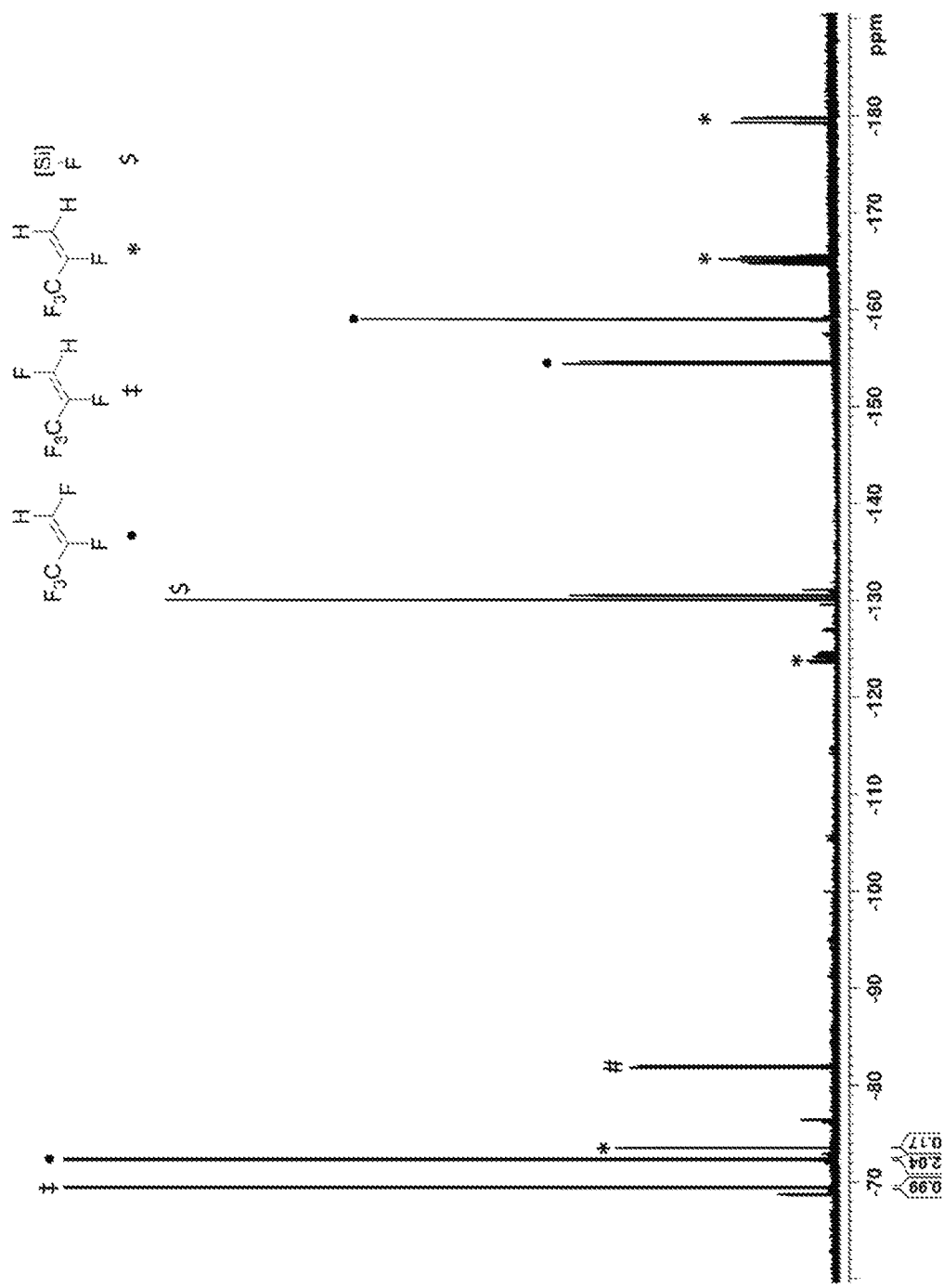
FIG. 4 depicts an $^{19}F$ NMR spectrum (282 MHz, $C_6D_6$) of the reaction of [Cu]—H with hexafluoropropene, where TMDS was the source of hydride (#=Vinylidene difluoride as a contaminant)

[(PPh$_3$)CuH]$_6$ (0.004 g, 0.0015 mmol or 0.0092 mmol of H$^-$) and tetramethyldisiloxane [TMDS] (0.135 g, 1.07 mmol) were placed in an NMR tube, dissolved in 0.6 mL of benzene-d$_6$ [C$_6$D$_6$] and capped with a rubber septum. HFP (3 mL, 1 atm) was then injected into the mixture and heated to 45° C. for ~24 hours. The reaction mixture was then analyzed by $^{19}$F NMR (see FIG. 4), which demonstrated >99% conversion of HFP. The normalized molar ratio of product distribution of 1225ye:1225ye(E) was 1:2, respectively. Trace amounts of 1234yf were also observed.

Reaction with Excess TMDS Vs Hexafluoropropene with Cu-PCp$_3$

[(PPh$_3$)CuH]$_6$ (0.004 g, 0.0015 mmol or 0.0092 mmol of H$^-$), TMDS (0.135 g, 1.07 mmol) and tricyclopentylphosphine (0.004 g, 0.016 mmol) were placed in an NMR tube, dissolved in 0.6 mL of benzene-d$_6$ [C$_6$D$_6$] and capped with a rubber septum. HFP (3 mL, 1 atm) was then injected into the mixture and heated to 45° C. for ~24 hours. A >99% conversion of HFP was observed. The normalized molar ratio of product distribution of 1225ye(E):1234yf was 1.2:1.5, respectively. Trace amounts of other impurities were also observed.

Reaction with Excess TMDS Vs HFP with Cu—P$^t$Bu$_3$

[(PPh$_3$)CuH]$_6$ (0.004 g, 0.0015 mmol or 0.0092 mmol of H$^-$), TMDS (0.135 g, 1.07 mmol) and tri(tertiary-butyl) phosphine (0.1 mL [10% v/v in hexane], 0.016 mmol) were placed in a NMR tube, dissolved in 0.6 mL of benzene-d$_6$ [C$_6$D$_6$] and capped with a rubber septum. HFP (3 mL, 1 atm) was then injected into the mixture and heated to 45° C. for ~24 hours. A >99% conversion of HFP was observed. The normalized molar ratio of product distribution of 1225ye (E):1234yf in a was 1.1:1, respectively. Trace amounts of other impurities were also observed.

Reaction with Excess TMDS Vs HFP with Cu—P(OEt)$_3$

[(PPh$_3$)CuH]$_6$ (0.004 g, 0.0015 mmol or 0.0092 mmol of H$^-$), TMDS (0.135 g, 1.07 mmol) and triethylphosphite (0.004 g, 0.016 mmol) were placed in a NMR tube, dissolved in 0.6 mL of benzene-d$_6$ [C$_6$D$_6$] and capped with a rubber septum. HFP (3 mL, 1 atm) was then injected into the mixture and heated to 45° C. for ~24 hours. A >99% conversion of HFP was observed. The normalized molar ratio of product distribution of 1234yf:(1,3,3,3-tetrafluoropropene):1234ze(E) was 7.5:1, respectively. Trace amounts of 1252zc were also observed.

Reaction with TMDS and Cu-dppf

Figure 5:
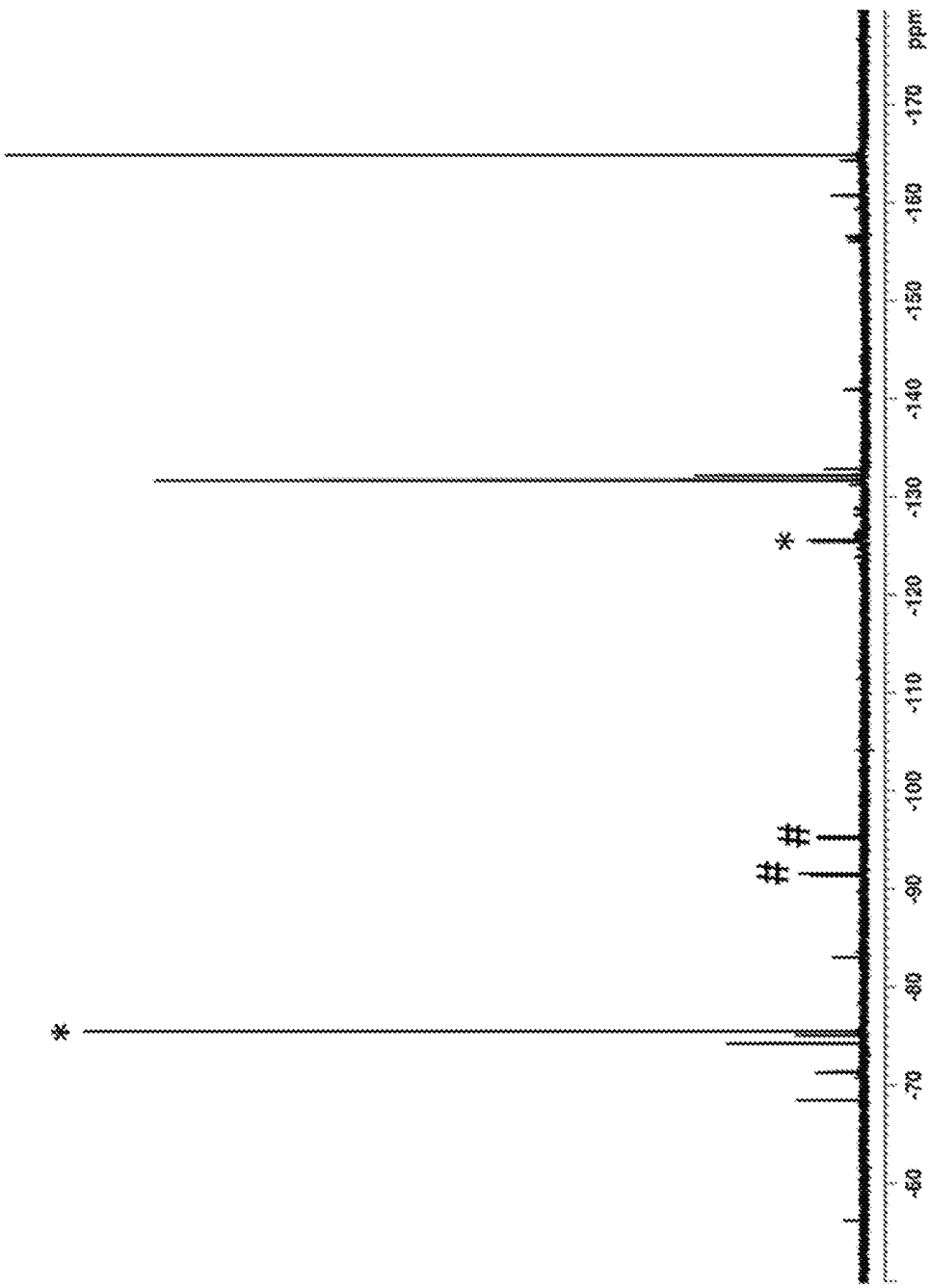
FIG. 5 depicts an $^{19}F$ NMR spectrum (282 MHz, $C_6D_6$) of the reaction of [Cu]—H 1,1'-bis(diphenylphosphino)ferrocene with hexafluoropropene, where TMDS was the hydride source (*=1234yf and #=1252zc)

[(PPh$_3$)CuH]$_6$ (0.020 g, 0.010 mmol or 0.061 mmol of H$^-$) and 1,1'-bis(diphenylphos-phino)ferrocene (0.035 g, 0.061 mmol) were placed in an NMR tube, dissolved in 0.5 mL of benzene-d$_6$ [C$_6$D$_6$] and 0.1 mL of TMDS and capped with a rubber septum. HFP (3 mL, 1 atm) was then injected into the mixture and left to sit at 25° C. for 10 minutes after which point it was heated to 50° C. for 18 hours. The reaction mixture was then analyzed by $^{19}$F NMR spectroscopy which demonstrated >99% conversion of HFP (FIG. 5). The normalized molar ratio of product distribution of 1234yf:1252zc was 2:1, respectively.

Reaction with TMDS and Cu-dppe

Figure 6:
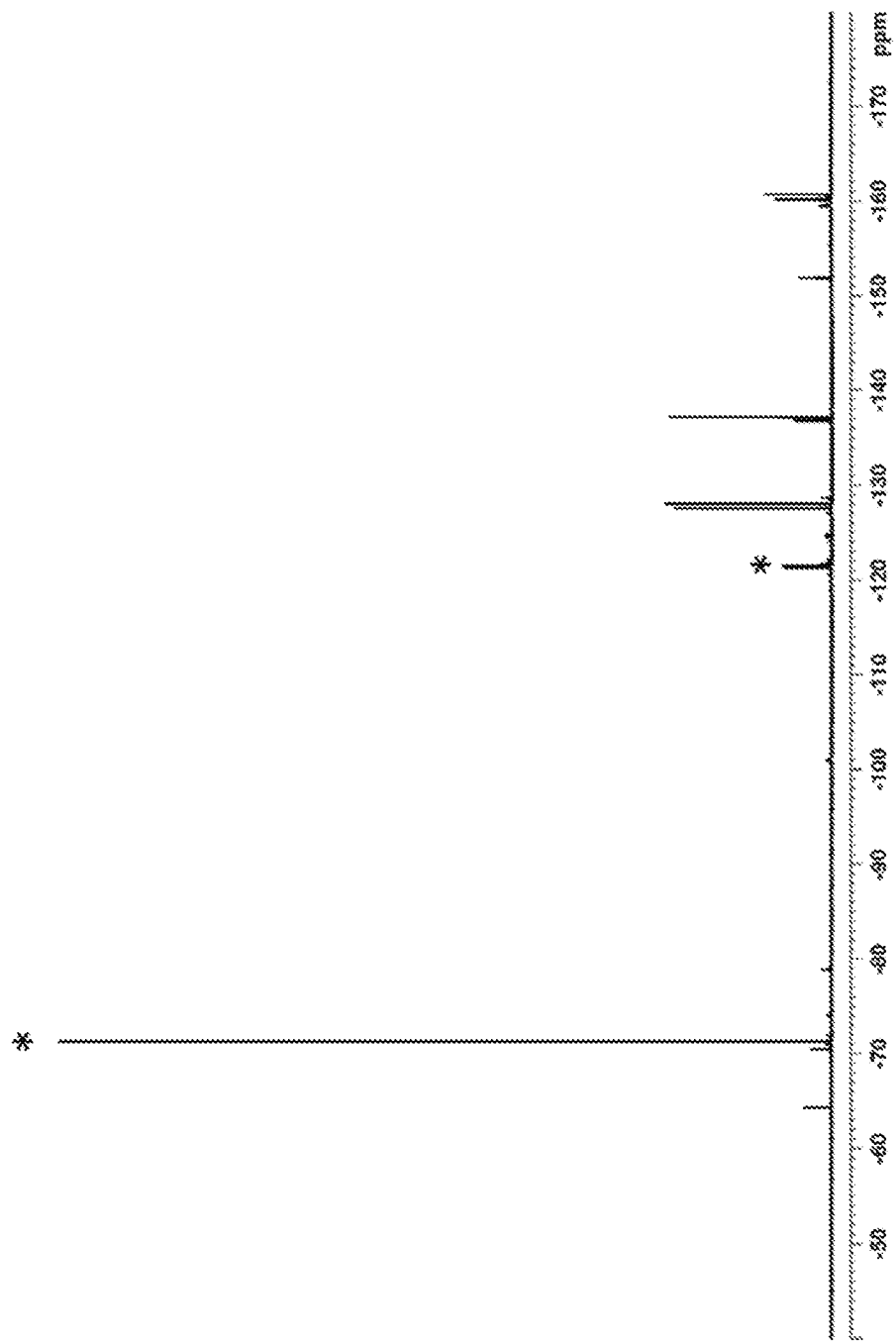
FIG. 6 depicts an $^{19}F$ NMR spectrum (282 MHz, $C_6D_6$) of the reaction of [Cu]—H 1,2-bis(diphenylphosphino)ethane with hexafluoropropene, where TMDS was the hydride source (*=1234yf)

[(PPh$_3$)CuH]$_6$ (0.020 g, 0.010 mmol or 0.061 mmol of H$^-$) and 1,2-bis(diphenylphosphino)ethane (dppe, 0.025 g, 0.061 mmol) were placed in an NMR tube, dissolved in 0.5 mL of benzene-d$_6$ [C$_6$D$_6$] and 0.1 mL of TMDS and capped with a rubber septum. Gaseous HFP (3 mL, 1 atm) was then injected into the mixture and left to sit at 25° C. for 10 minutes, after which point it was heated to 50° C. for 18 hours. The reaction mixture was then analyzed by $^{19}$F NMR spectroscopy, which demonstrated >99% conversion of HFP (FIG. 6). The major product was 1234yf.

The results are summarized in Table 1.

|  | No Silane | PhMe$_2$SiH | PMHS | TMDS |
|---|---|---|---|---|
| No added ligand |  |  |  | 1225ye:1225ye(E) 1:2 |
| PPh$_3$ | Minor Products 1225ye & 1225ye(E) | 1225ye(E):1225ye:1234yf 2.2:1.6:1 | 1225ye(E):1234yf 1.5:1 |  |
| PCp$_3$ |  |  |  | 1225ye(E):1234yf 1.2:1.5 |
| P(t-Bu)$_3$ |  |  |  | 1225ye(E):1234yf 1.1:1 |
| P(OEt)$_3$ |  |  |  | 1234yf:1234ze(E) 7.5:1 Minor Product 1252zc |
| dppf |  |  |  | 1234yf:1252zc 2:1 |
| dppe |  |  |  | 1234yf |

It has been demonstrated here that by varying reaction conditions with [Cu]—H, and changing the silane and phosphine ligand, different product ratios are obtained. The ratios shown in Table 1 are molar ratios of the major products. Where appropriate, minor products are indicated without ratios.

Figure 7:
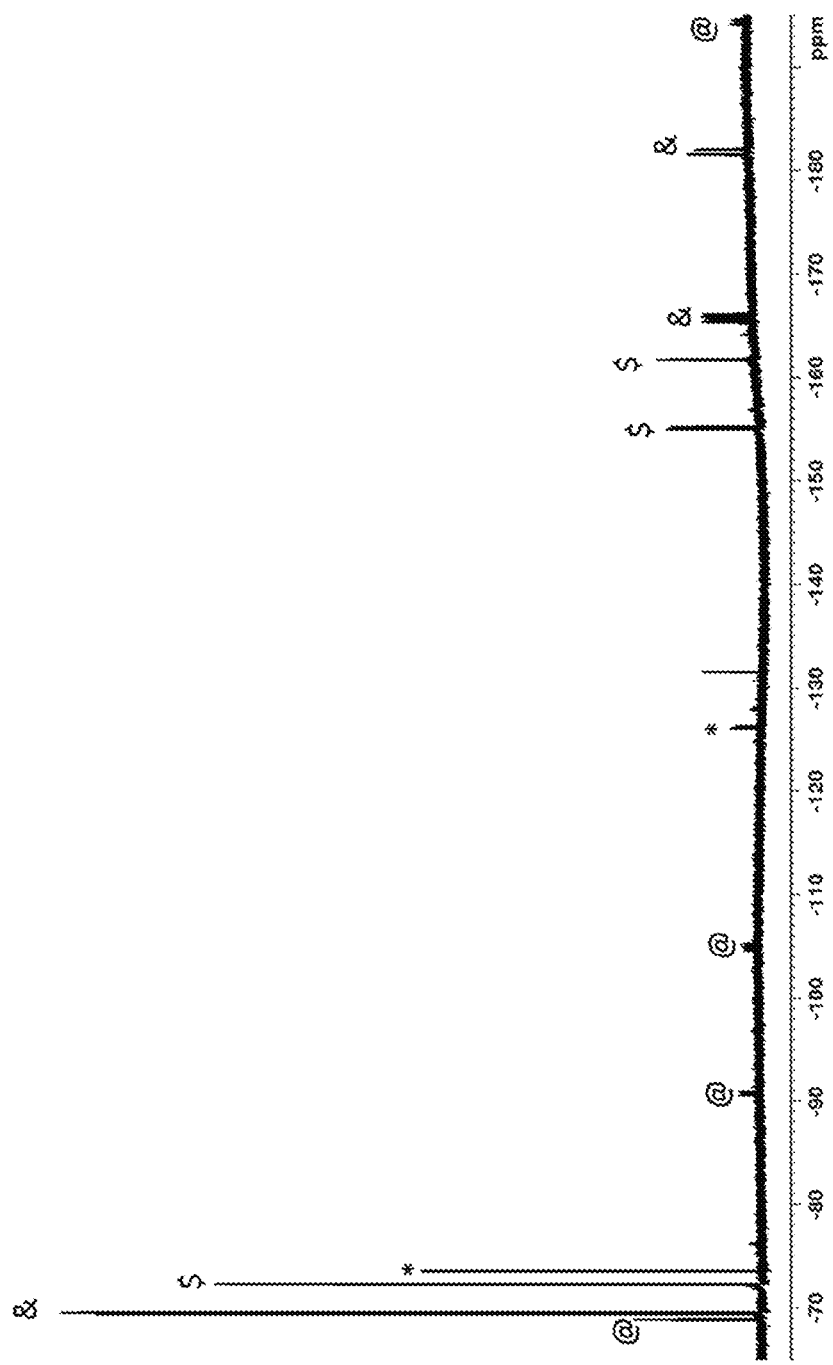
FIG. 7 depicts an $^{19}F$ NMR spectrum (282 MHz, $C_6D_6$) of a 1 ml sample of a scale-up reaction of [Cu]—H 1,2-bis(diphenylphosphino)ethane with hexafluoropropene, where TMDS was the hydride source, after 3 hours ($=1225ye, &=1225ye(E), *=1234yf, and @=HFP)
Figure 8:
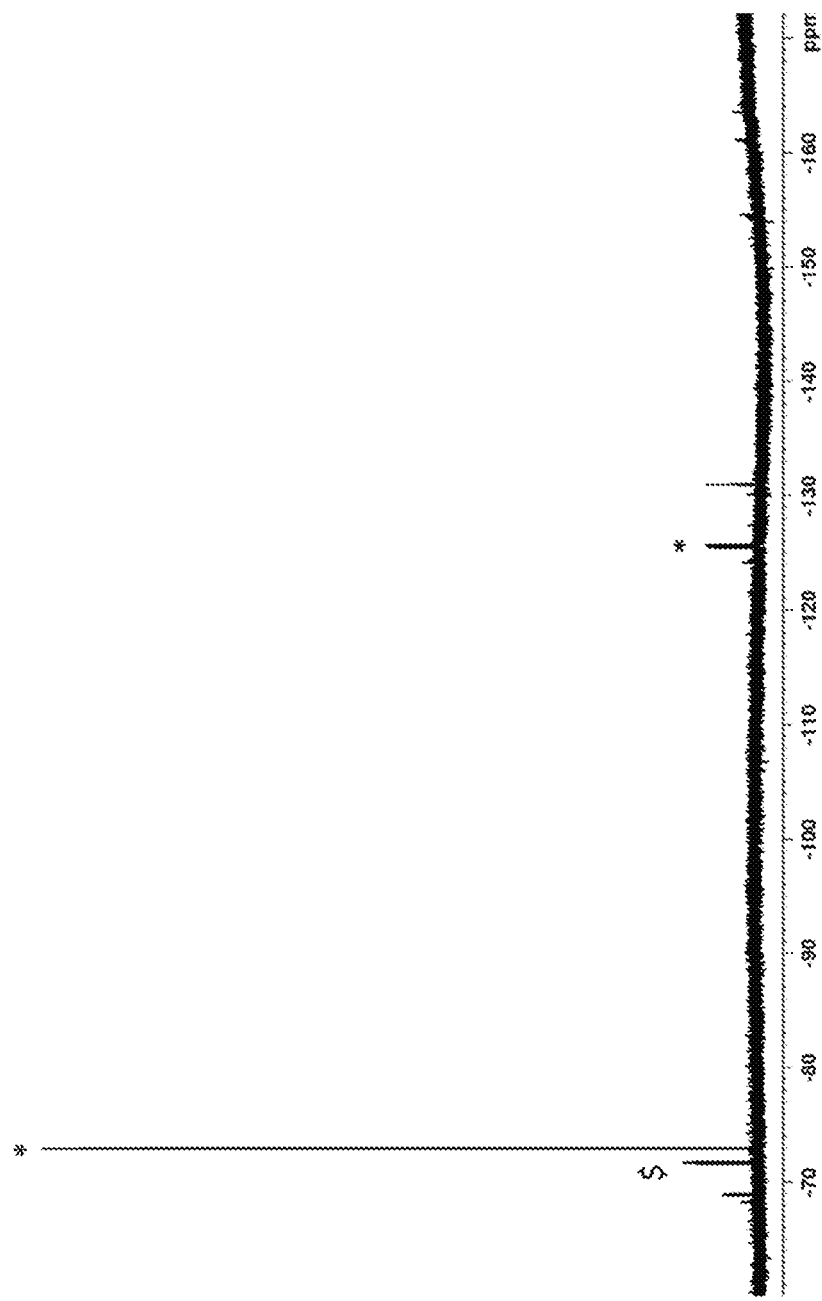
FIG. 8 depicts an $^{19}F$ NMR spectrum (282 MHz, $C_6D_6$) of a 1 ml sample of the scale-up reaction from FIG. 7, after 7 hours ($=1225ye and *=1234yf,)

Scale-Up of Hydrodefluorination of Hexafluoropropene with Cu-Dppe and TMDS:

[(PPh$_3$)CuH]$_6$ (0.100 g, 0.300 mmol or 1.84 mmol of H—) and dppe (0.732 g, 1.84 mmol) were placed in a 1 L round bottom flask, dissolved in 20 mL of benzene and TMDS (12.5 mL, 122.4 mmol) and capped with a rubber septum. Gaseous HFP (1 L, 1 atm) was loaded into a balloon and injected into the mixture and left to sit at 50° C. for 8 hours. The reaction mixture was then analyzed by $^{19}$F NMR spectroscopy at 3 hours (FIG. 7) and at 7 hours (FIG. 8), which demonstrated >99% conversion of hexafluoropropene [HFP]. Calculated turn-over frequency (TOF): $2.0 \times 10^{-3}$ s$^{-1}$.

Example 2: Hydrofluoroalkene Production from Tetrafluoroethylene

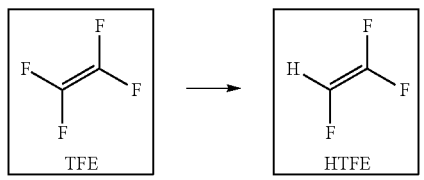 [SMILES: FC(F)=C(F)F ; FC=C(F)F]

Reaction with Excess TMDS Vs TFE with Cu-PCp$_3$

[(PPh$_3$)CuH]$_6$ (0.004 g, 0.0015 mmol or 0.0092 mmol of H$^-$), TMDS (0.135 g, 1.07 mmol) and tricyclopentylphosphine (0.004 g, 0.016 mmol) were placed in a NMR tube, dissolved in 0.6 mL of benzene-d$_6$ [C$_6$D$_6$] and capped with a rubber septum. Gaseous TFE (3 mL, 1 atm) was then injected into the mixture and heated to 80° C. for ~24 hours. The reaction mixture was then analyzed by $^{19}$F NMR (see FIG. 9), which demonstrated minor conversion of TFE to trifluoroethylene [HTFE] as minor product.

Reaction with Excess TMDS Vs TFE with Cu—P(OEt)$_3$ and KO$^t$Bu as Additive

[(PPh$_3$)CuH]$_6$ (0.004 g, 0.0015 mmol or 0.0092 mmol of H$^-$), TMDS (0.135 g, 1.07 mmol), triethylphosphite (0.004 g, 0.016 mmol) and potassium tertiary-butoxide (0.135 g, 1.00 mmol) were placed in an NMR tube, dissolved in 0.6 mL of benzene-d$_6$ [C$_6$D$_6$] and capped with a rubber septum. TFE (3 mL, 1 atm) was then injected into the mixture and heated to 80° C. for ~24 hours. Minor conversion of TFE to HTFE was observed.

Example 3: Hydrofluoroalkene Production from Trifluoromethyl Trifluorovinyl Ether

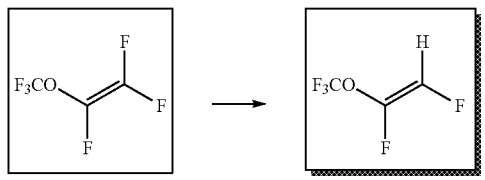

Reaction with Excess TMDS Vs FMVE with PCp$_3$ and KO$^t$Bu as Additive

[(PPh$_3$)CuH]$_6$ (0.004 g, 0.0015 mmol or 0.0092 mmol of H$^-$), TMDS (0.135 g, 1.07 mmol), tricyclopentylphosphine (0.004 g, 0.016 mmol) and potassium tertiary-butoxide (0.135 g, 1.00 mmol) were placed in an NMR tube, dissolved in 0.6 mL of benzene-d$_6$ [C$_6$D$_6$] and capped with a rubber septum. Gaseous trifluoromethyl trifluorovinyl ether (FMVE) (2 mL, 1 atm) was then injected into the mixture and heated to 25° C. for 10 minutes. A >99% conversion of FMVE was observed, with the major product being (E)-trifluoromethyl-1,2-difluorovinyl ether.

Example 4: Hydrofluoroalkene Production from Iodotrifluoroethylene

Reaction with Cu-dppe and Red-Al

[(PPh$_3$)CuH]$_6$ (0.020 g, 0.010 mmol or 0.061 mmol of H$^-$), 1,2-bis(diphenylphosphino)ethane (0.025 g, 0.061 mmol) and a solution of sodium bis(2-methoxyethoxy) aluminum hydride, 60 wt. % in toluene [Red-Al] (71 μL, 0.22 mmol) were placed in an NMR tube, dissolved in 0.5 mL of benzene and capped with a rubber septum. Liquid iodotrifluoroethylene [ITFE] (10 μL, 0.11 mmol) was then injected into the cooled mixture, 0° C., and then warmed to 25° C. for 10 minutes. The reaction mixture was then analyzed by $^{19}$F NMR spectroscopy (FIG. 10). The normalized molar ratio of product distribution of trifluoroethylene [HTFE]: cis-1,2-difluoroethylene:trans-1,2-difluoroethylene was 1:1:6 respectively.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A process for hydrodehalogenation of a fluoroalkene comprising treating a fluoroalkene with a hydride source and a catalyst of Formula VIII $$L_xM_yH_z \qquad \text{VIII}$$

where each L is, independently, Bipy, Phen, or a monodentate, bidentate, tridentate, or tetradentate phosphorous, nitrogen, oxygen, sulfur or carbon-based ligand or combination thereof, of the general formula PR$_3$, NR$_3$, SR$_2$, OR$_2$, :CR$_2$ where each R is independently; H, alkyl, aryl, silyl, alkoxy, amino, or halogen;

M is a Group 11 metal; and x is an integer from 1 to 4;

y is 1;

z is an integer from 1 to 4; and the sum of z+x is less than or equal to 4.

2. The process of claim 1, wherein the fluoroalkene is a compound of Formula I and the product is a compound of Formula IIa, a compound of Formula IIb, or any combination thereof:

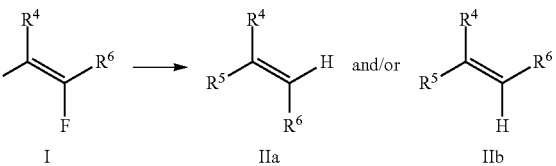

where each of R$^4$, R$^5$ and R$^6$ are each independently H, halogen, alkyl, alcohol, OR', NR'$_3$, SH, SW, fluorothioether, silyl, =CR'$_2$, —C(R')=CR', —C≡CR', phenyl, —C(O)R', —C(O)H, —OC(O)OR', —C(O)OR', —C≡N, —N≡C, —NO₂, —C₅H₄N, —S(O)R', —S(O)₂R', —SC≡N, —B(OR')₂, or a fluorovariant thereof in which one or more C—H bond is replaced with a C—F bond, where R' is an alkyl or alkenyl group.

3. The process of claim 1, wherein the fluoroalkene is a compound of Formula Ia and the product is a compound of Formula IIIa, Formula IIIb, Formula IIIc, Formula IVa, Formula IVb, or any combination of two or more thereof:

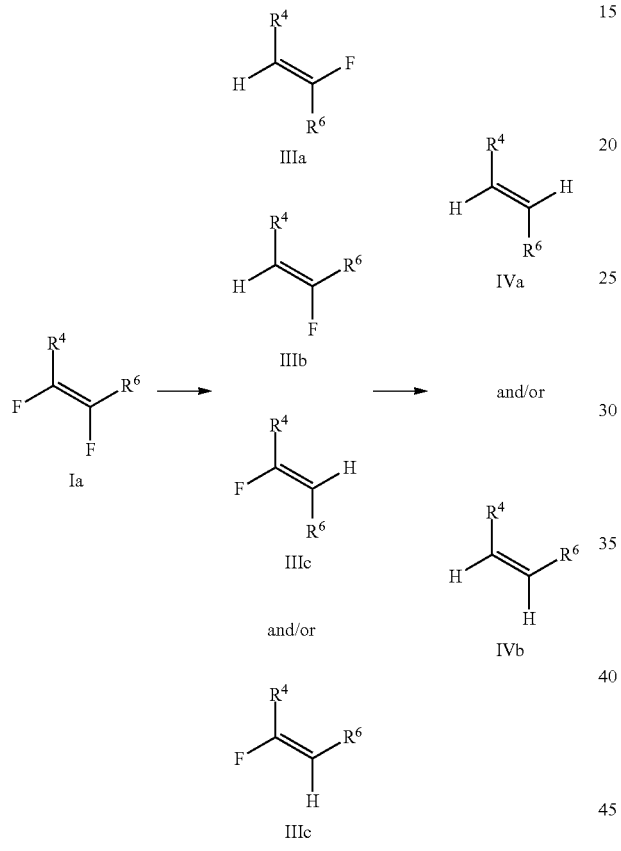

where each of R⁴ and R⁶ are each independently H, halogen, alkyl, alcohol (OH), ether (OR), amine (NR₃), thiol (SH), thioether (SR), fluorothioether, silyl, allene (=CR₂), vinyl (—C(R)=CR₂), alkynyl (—C≡CR), Phenyl (Ph), carbonyl (—C(O)R), aldehyde (—C(O)H), carbonate (—OC(O)OR), ester (—C(O)OR), nitrile (—C≡N), isonitrile (—N≡C), nitro (—NO₂), pyridyl (—C₅H₄N), sulfinyl (—S(O)R), sulfonyl (—S(O)₂R), thiocyanate (—SC≡N), boronate (—B(OR)₂), or a fluorovariant thereof in which one or more C—H bond is replaced with a C—F bond.

4. The process of claim 1, wherein the fluoroalkene is a compound of Formula Ib and the product is a compound of Formula Va, Formula Vb, Formula Vb, Formula VIa, Formula VIb, Formula VIc, Formula VII, or any combination of two or more thereof:

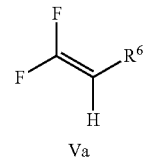
Va

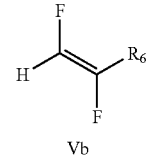
Ib → Vb and/or

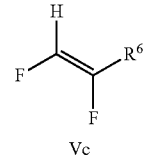
Vc

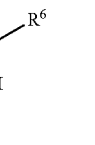
VIa

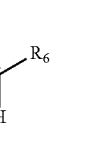
VIb and/or →  VII

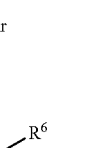
VIc where is H, halogen, alkyl, alcohol (OH), ether (OR), amine (NR₃), thiol (SH), thioether (SR), fluorothioether, silyl, allene (=CR₂), vinyl (—C(R)=CR₂), alkynyl (—C≡CR), Phenyl (Ph), carbonyl (—C(O)R), aldehyde (—C(O)H), carbonate (—OC(O)OR), ester (—C(O)OR), nitrile (—C≡N), isonitrile (—N≡C), nitro (—NO₂), pyridyl (—C₅H₄N), sulfinyl (—S(O)R), sulfonyl (—S(O)₂R), thiocyanate (—SC≡N), boronate (—B(OR)₂), or a fluorovariant thereof in which one or more C—H bond is replaced with a C—F bond.

5. The process according to claim 1, wherein the each L is independently P(OEt)₃, PPh₃, PCp₃, Bipy, Phen, tmeda, Triphos, Diphos, bis(diphenylphosphino)benzene, IPr (1,3-Bis(2,6-diisopropylphenyl)-imidazol-2-ylidene), or SIMes (1,3-Bis(2,4,6-trimethylphenyl)-2-imidazolidinylidene).

6. The process according to claim 1, wherein M is CuI or CuII.

7. The process according to claim 1, wherein the catalyst is $(PPh_3)_3CuH$ or $(PPh_3)_2CuH$.

8. The process according to claim 1, wherein the hydride source is a silane.

9. The process of claim 8, wherein the silane is $R^1R^2R^3SiH$, where $R^1$, $R^2$, $R^3$ are each, independently, H, Alk(alkyl), Ar(aryl), $SiR_3$ (silyl), OR (alkoxy), $NR_2$ (amino) or halogen.

10. The process according to claim 1, wherein the process is used to produce Z-1,2,3,3,3-pentafluoroprop-1-ene [HFO-1225ye], E-1,2,3,3,3-pentafluoroprop-1-ene [HFO-1225ye (E)], 2,3,3,3-tetrafluoroprop-1-ene [HFO-1234yf], 1,3,3,3-tetrafluoropropene [HFO-1234ze(E)] or 1,1-difluoropropene [HFO-1252zc] from hexafluoropropene [HFP].

* * * * *

UNITED STATES PATENT AND TRADEMARK OFFICE
CERTIFICATE OF CORRECTION

Page 1 of 1

PATENT NO. : 10,774,021 B2
APPLICATION NO. : 16/329633
DATED : September 15, 2020
INVENTOR(S) : Baker et al.

It is certified that error appears in the above-identified patent and that said Letters Patent is hereby corrected as shown below:

In the Claims

Claim 4, Column 16, Line 51:
Now reads: "where is H,"
Should read: --where $R^6$ is H,--

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*